(12) United States Patent
Champion et al.

(10) Patent No.: US 6,749,832 B2
(45) Date of Patent: Jun. 15, 2004

(54) LABELLED ASCORBIC ACID DERIVATIVES

(75) Inventors: Susan Champion, Tring (GB); Richard Pither, Amersham (GB)

(73) Assignee: Amersham PLC, Buckinghamshire (GB)

(*) Notice: Subject to any disclaimer, the term of this patent is extended or adjusted under 35 U.S.C. 154(b) by 0 days.

(21) Appl. No.: 10/168,714

(22) PCT Filed: Dec. 22, 2000

(86) PCT No.: PCT/GB00/04930
§ 371 (c)(1),
(2), (4) Date: Sep. 16, 2002

(87) PCT Pub. No.: WO01/47564
PCT Pub. Date: Jul. 5, 2001

(65) Prior Publication Data
US 2003/0153736 A1 Aug. 14, 2003

(30) Foreign Application Priority Data
Dec. 23, 1999 (EP) .............................. 99310462

(51) Int. Cl.$^7$ .................. A61K 51/00; A61M 36/14
(52) U.S. Cl. .................. 424/1.65; 424/1.11; 424/9.1; 424/1.85; 424/1.81; 549/315; 534/14
(58) Field of Search .............................. 424/1.11, 1.65, 424/1.81, 1.89, 9.1, 1.37, 1.69, 1.73, 1.85, 9.3, 9.4, 9.5, 9.6, 9.7, 9.8; 534/7, 10–16; 549/315, 200, 201, 205, 263, 295, 313, 314; 514/449

(56) References Cited

U.S. PATENT DOCUMENTS

| 4,455,291 A | 6/1984 | Tweedle |
| 4,707,353 A | * 11/1987 | Bugaj et al. ............... 424/1.11 |
| 5,032,610 A | 7/1991 | Borretzen et al. |
| 5,202,109 A | 4/1993 | Fritzberg et al. |

FOREIGN PATENT DOCUMENTS

WO   WO 97/06824 A   2/1997

OTHER PUBLICATIONS

Vollhardt (1987), Organic Chemistry, pp. 368–375.*
Liu et al, He Huaxue Yu Fangshe Huaxue (1999), 21(1), 28–34.*
Horner et al, Int. J. Plant Sci. (Nov. 2000), 161(6), 861–868.*
Keates et al, Phytochemistry (Feb. 2000), 53(4), 433–440.*
J. Wilson, et al. "High–affinity sodium–dependent uptake of ascorbic acid by rat osteoblasts" J. Membr. Biol. (1989), 111(1) pp. 83–91, (abstract submitted).
F. Yamamoto, et al. "Positron labeled antioxidants: synthesis and tissue biodistribution of 6–deoxy–6–'18F!fluoro–L–ascorbic acid" Appl. Radiat. Isot. (1992), 43(5) pp. 633–639, (only abstract submitted).
F. Yamamoto, et al. "6–Deoxy–6–'18F!fluoro–L–ascorbic acid. Tissue biodistribution is ascorbic acid–deficiency and RG–C6 glioma bearing rats" Radioisotopes (1995), 44(2) pp. 93–98, (abstract submitted).

* cited by examiner

Primary Examiner—Dameron L. Jones
(74) Attorney, Agent, or Firm—Li Cai

(57) ABSTRACT

Compounds of formula (I) where: $X^1$ is OH or SH or $NH_2$ or —L-Z; $X^2$ and $X^3$ are the same or different and each is H, $C_{1-4}$ alkyl, benzyl a protecting group or —L-Z, $X^4$ is H or $C_{1-4}$ alkyl, L is a linker comprising a chain of 0–10 atoms, Z is a group comprising a detectable moiety which comprise at least one detectable moiety are useful in the diagnosis and prognosis and radiotherapy of metastatic bone disease.

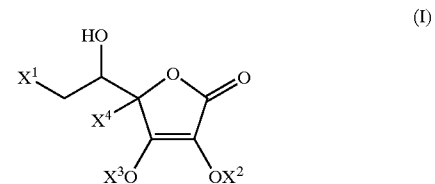

(I)

14 Claims, No Drawings

LABELLED ASCORBIC ACID DERIVATIVES

FIELD OF INVENTION AND BACKGROUND TO THE INVENTION

The present invention relates to a class of compounds useful in the diagnosis or radiotherapy of metastatic bone disease, pharmaceutical formulations containing them, their use in the diagnosis of disease and monitoring of disease progression and treatment, and methods for their preparation.

CURRENT BONE IMAGING AGENTS

Bone is a common site of metastatic disease with around 70–80% of breast and prostate cancers metastasising to bone. Lung, thyroid, kidney and bladder cancers can also metastasise to bone. Once tumour cells are implanted in the bone marrow they release biochemical mediators which activate osteoblasts. The osteoblastic response detected on a bone scan is a secondary response. Osteoblasts are bone-producing cells implicated in the pathology associated with metastatic bone disease. Activated osteoblasts produce large quantities of collagen that, in addition to its structural role, is important in osteoblast differentiation.

Diagnosis of metastatic bone disease may be achieved by one of four methods—radiography, CT scanning, radioisotope bone scan or MRI. The radioisotope bone scan has been the standard initial imaging method for the past 25 years. The usual tracer for bone scans is $^{99m}$Tc-methylene diphosphonate ($^{99m}$Tc-MDP). $^{99m}$Tc-HMDP (hydroxymethylenediphosphonate) and $^{99m}$Tc-HEDP (1-hydroxyethyl-1,1-diphosphonate) may also be used. These agents have broadly similar characteristics. Around 550–750 MBq (15–20 mCi) is injected and high bone uptake (30–50% of the injected dose) occurs within 2 hours. Scans are typically carried out 3–4 hr post administration of agent, due to slow clearance from the blood and/or tissue. Whole body imaging (anterior/posterior) with an acquisition time of 20–30 min produces images of high quality, good resolution and high sensitivity/specificity.

$^{99m}$Tc-MDP is adsorbed onto the calcium of hydroxyapatite in bone. This process is influenced by the levels of osteoblastic activity and by skeletal vascularity. There is preferential uptake at sites of active bone formation, and the amount of accumulation is sensitive to the level of blood flow. The bone scan therefore reflects the metabolic reaction of bone to the disease process, regardless of whether the metabolic activity is neoplastic, traumatic or inflammatory in nature. Thus, the tracer accumulates at any site of elevated bone turnover and the scan is therefore very non-specific.

Osteoblastic metastases resulting in hot spots are detected regardless of size but a cold (photopenic) spot, caused as a result of osteolytic disease, has to reach a certain size to be detected.

The general advantages of the radioisotope scan are a large field of view, low cost, low morbidity, high sensitivity for detection of skeletal metastases, ease of performance on any patient and relatively low total body dose.

DISADVANTAGES AND PROBLEMS ASSOCIATED WITH CURRENT RADIOISOTOPE BONE IMAGING AGENTS

Tracer accumulation may occur at any skeletal site with an elevated rate of turnover and in this case does not provide functional or vascular information. As the bone scan has low specificity, the nature of an abnormality cannot be determined from the scan, hence benign and malignant lesions often cannot be distinguished. The technique is also anatomically imprecise. Binding to bone can still occur after tumour cells are dead as collagen is still produced. Consequently there is no distinction between bone healing and tumour progression, with the result that it is difficult to monitor effects of treatment. An increase in the uptake of $^{99m}$Tc-MDP due to bone healing can be seen up to 6 months after treatment and is known as the flare response.

There is no net production of collagen in osteolytic disease, hence false negatives occur—some or all lesions are missed. Such negative scans need to be re-evaluated with clinical and lab findings. If these are non-conclusive then radiography is used, if this is still non-conclusive then bone biopsy or MRI are used.

The low specificity of $^{99m}$Tc-MDP means the nature of the abnormality e.g. benign vs malignant lesion cannot be detected. In a patient with known primary tumours, multiple hot spots in the bone scan indicate metastases. However 50% of these hot spots could be other non-metastatic lesions. Therefore a lack of specificity observed with $^{99m}$Tc-MDP means that positive scans often have to be accompanied by radiographic correlation (a positive radiograph confirms the presence of metastases as the bone scan is more sensitive, but a negative radiograph does not rule them out).

MRI is sometimes chosen, mainly due to its ability to demonstrate abnormalities in bone marrow. However, MRI often cannot distinguish between changes that are due to treatment, fracture and tumour and is less well suited to scanning long bones.

Despite the problems associated with the current radioisotope bone imaging agents, their unique features make them the first choice for screening for metastases in a symptomatic patients. However, a negative scan should always be re-evaluated with clinical and laboratory findings due to the possibility of false negatives. Furthermore, the possibility of a non-metastatic cause of an abnormal scan always needs to be considered. Non-conclusive findings generally lead to supplementary examination with radiography. If diagnosis is still unclear, bone biopsy or MRI will be performed.

There is therefore a need for a diagnostic imaging agent which has specificity for metastatic bone lesions (as opposed to other lesion types), and which can give clinically useful information in a single imaging protocol, without the need for additional testing.

Skeletal metastases may respond to chemotherapy or hormone therapy used to treat the primary tumour. They may also respond to radiation or to agents designed to block bone resorption such as the new class of bisphosphonate (BP) drugs. Bisphosphonates have potent inhibitory effects on bone resorption and are the treatment of choice for hypercalcaemia of malignancy. Treatment can lead to a reduction in the number and rate of skeletal complications in multiple myeloma and advanced breast cancer and can delay the onset of progressive disease in bone following palliative chemotherapy in breast cancer and myeloma. BPs also relieve metastatic bone pain in around 50% of patients but this requires intravenous injection as BPs are not potent enough and not tolerated well when taken orally. Response to treatment can be measured by biochemical markers e.g. excretion of collagen cross-links. Radioisotopes are also used in the treatment of bone metastases [Ben-Josef & Porter, Ann Med. 29, 31–35, (1997); Lewington, Phys Med Biol. 41, 2027–2042 (1996)]. $^{89}$Sr has been successfully used in pain palliation. Other bone-seeking isotopes include $^{32}$P (side effect of myelotoxicity), $^{153}$Sm (complexed with EDTMP) and $^{186}$Re (complexed with HEDP).

$^{14}$C and $^{3}$H-labelled ascorbic acid derivatives are known. Yamamoto et al [Appl. Radiat. Isot. 43, 633–639 (1992)] have described the preparation of 6-deoxy-6-[$^{18}$F]fluoro-L-ascorbic acid ($^{18}$F-DFA), i.e. an ascorbic acid derivative labelled with the positron emitting isotope [$^{18}$F] via nucleophilic displacement of a cyclic sulfate with fluoride ion. The biodistribution of this compound has been studied in rats and fibrosarcoma-bearing mice. Yamamoto et al [Radioisotopes, 44, 93–98 (1995)] have also studied the biodistribution of $^{18}$F-DFA in Wistar normal rats, ODS rats unable to synthesise ascorbic acid, and Wistar male rats implanted with RG-G6 glioma intracerebrally, and [Nucl. Med. Biol., 23, 479–486 (1996)] the in vivo uptake and distribution of $^{18}$F-DFA in rat brains following postischemic reperfusion.

The bone uptake reported for $^{18}$F-DFA is very low and there is no suggestion that labelled ascorbic acid derivatives could be useful for either bone imaging in general, or metastatic bone disease imaging in particular. In addition, $^{18}$F has a half life of 1.8 hours, and is therefore only usable for a few hours (including synthesis and purification time). Hence any clinical use of such PET (positron emission tomography) agents is limited to a very restricted number of medical sites which possess a cyclotron on site.

SUMMARY OF THE INVENTION

The invention includes diagnostic agents for the detection and monitoring of metastatic bone disease as well as radiotherapy of such disease. The agents comprise a modified ascorbic acid labelled with a detectable moiety suitable for external imaging (e.g. by scintigraphy or MRI), such as a radionuclide or a paramagnetic metal ion.

Unmodified ascorbic acid has the formula:

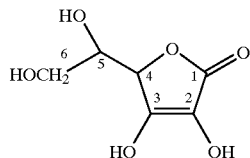

The agents of the present invention act by accumulating in osteoblast cells present at sites of increased bone turnover. These sites include areas of hyperproliferation associated with metastatic bone disease, as well as other bone pathologies. As the ascorbic acid derivatives are only taken up by osteoblasts at active lesions, they are of high diagnostic and prognostic value for osteoblastic lesions and allow rapid monitoring of disease progress. The use of ascorbates may also prevent the occurrence of false negative scans through visualisation of lytic lesions due to associated osteoblastic activity and also allow early diagnosis of small lesions due to the specific uptake mechanism. Uptake into normal bone will occur and will be useful for localising the lesion site, where uptake will be greatly increased.

DETAILED DESCRIPTION OF THE INVENTION

In a first aspect, the present invention provides a compound of formula:

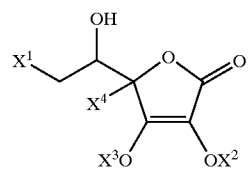

where: $X^1$ is OH or SH or $NH_2$ or -L-Z;

$X^2$ and $X^3$ are the same or different and each is H, $C_{1-4}$ alkyl, $C_{1-4}$ fluoroalkyl, benzyl, a protecting group or -L-Z;

$X^4$ is H or $C_{1-4}$ alkyl;

L is a linker comprising a chain of 0–10 atoms;

Z is a group comprising a detectable moiety;

provided that the compound comprises at least one detectable moiety.

$X^1$ is preferably -L-Z. $X^2$ and $X^3$ are preferably H or $C_1$ alkyl, most preferably both $X^2$ and $X^3$ are H. $X^4$ is preferably H or $C_1$ alkyl, most preferably H. The linker L is suitably a chain of 0–10 atoms of formula $(A)_m$ where: A is $-CR_2-$, $-CR=CR-$, $-C\equiv C-$, $-NRCO-$, $-CONR-$, $-O(CO)-$, $-(CO)O-$, $-SO_2NR-$, $-NRSO_2-$, $-OCR_2-$, $-SCR_2-$, $-NRCR_2-$, a $C_{4-8}$ cycloheteroalkylene group, a $C_{4-8}$ cycloalkylene group, a $C_{5-12}$ arylene group or a $C_{3-12}$ heteroarylene group;

m is an integer of value 0 to 10;

each R group is independently chosen from H, $C_{1-4}$ alkyl, $C_{1-4}$ alkenyl, $C_{1-4}$ alkynyl, $C_{1-4}$ alkoxyalkyl or $C_{1-4}$ hydroxyalkyl.

L preferably comprises a 0–4 atom chain.

Preferred compounds have the defined stereochemistry shown:

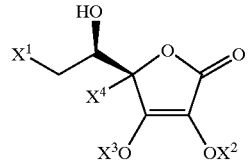

with $X^1$–$X^4$, L and Z as defined above.

The "detectable moiety" is a substance suitable for external imaging after human administration and can be a radionuclide, where the radionuclide is a gamma-emitter that emits gamma radiation that can penetrate soft tissue, a beta-emitter or a low energy X-ray emitter. Radionuclides which are positron emitters such as $^{11}$C and $^{18}$F are outside the scope of the present invention. $^{3}$H and $^{14}$C are not suitable radioisotopes for either external imaging or radiotherapy, and are hence also outside the scope of the present invention. The detectable moiety can also be: one or more hyperpolarised atom(s) such as the $^{13}$C carbon atom of a $^{13}$C-enriched compound for MRI imaging; a paramagnetic moiety as a contrast agent for MRI (e.g. certain metal ions such as gadolinium(III), or manganese (II)); a radiopaque moiety such as iopamidol for X-ray contrast imaging (computer assisted tomography) or an ultrasound contrast agent. Preferably, the detectable moiety is either a radionuclide γ-emitter such as $^{123}$I, $^{99m}$Tc, $^{111}$In, $^{113m}$In or $^{67}$Ga or a hyperpolarised material. Most preferred radionuclide γ-emitters are $^{123}$I and $^{99m}$Tc, especially $^{99m}$Tc. It is also envisaged that certain radionuclides will confer useful radiotherapeutic properties on the labelled ascorbic acid. Thus for example $^{90}$Y, $^{89}$Sr, $^{186}$Re, $^{188}$Re, $^{125}$I, $^{131}$I, $^{32}$P or $^{33}$P labelled ascorbic acids could be used in the treatment of metastatic bone disease. In such applications the therapeutic effect would be due to the local targeted radioactive dose delivered to specific cells, as opposed to any pharmacological effect due to the ascorbic acid. Whichever detectable moiety is chosen, it is strongly preferred that it is bound to the ascorbic acid in such a way that it does not undergo facile metabolism (either in vivo or in vitro), since such metabolism would result in the biodistribution of the detectable moiety no longer reflecting that of the ascorbic acid.

When the detectable moiety is a hyperpolarised $^{13}$C atom, this atom may form an integral part of the chemical structure of the ascorbic acid, or can be attached as a supplemental group. Most other detectable moieties must form supplemental structural elements, and can be attached at the 2, 3, 4, 5 or 6-positions of the ascorbic acid derivative. Preferred positions for the detectable moiety are the 2, 3 and 6-positions, with the 6-position being most preferred.

By the term 'protecting group' is meant those moieties known to those skilled in the art which would prevent metabolic modification of the ascorbic acid moiety. This may include alkyl, alkoxyalkyl, benzyl or acyl groups. The protecting group may also function to prevent any oxidation or other chemical degradation process of the ascorbic acid hydroxyl groups, and for such purposes is chosen to be sufficiently labile so that the protecting group is cleaved during the labelling or radiolabelling process.

When the detectable moiety is a radioactive or paramagnetic metal, the metal ion is always complexed. This metal complex is preferably achieved by attaching a ligand which binds strongly to metals to the ascorbic acid moiety. Such strongly metal-binding ligands include monodentate compounds which bind well to transition metals such as phosphines, isonitriles or hydrazides, and polydentates such as chelating agents. The ligand-ascorbic acid conjugate is complexed with the radioactive or paramagnetic metal ion, and the metal binds selectively to the ligand, giving a metal complex of the ligand linked to the ascorbic acid derivative.

The chelating agents of the present invention comprise 2–10 metal donor atoms covalently linked together by a non-coordinating backbone. Suitable bidentate chelating agents include bisphosphonates and diphosphines. Bisphosphonate complexes of radiometals have the advantage that the radiometal complex is already targeted to the bone in vivo. Preferred chelating agents have 4–8 metal donor atoms and have the metal donor atoms in either an open chain or macrocyclic arrangement or combinations thereof. Most preferred chelating agents have 4–6 metal donor atoms and form 5- or 6-membered chelate rings when coordinated to the metal centre. Such polydentate and/or macrocyclic chelating agents form stable metal complexes which can survive challenge by endogenous competing ligands for the metal in vivo such as transferrin or plasma proteins. The metal complex should also preferably be of low lipophilicity (since high lipophilicity is often related to non-specific uptake), and exhibit low plasma protein binding since plasma bound label again contributes to undesirable high, non-specific background for the imaging agent.

Examples of suitable chelating agents are diaminedioximes (U.S. Pat. No. 4,615,876) or such chelates incorporating amide donors (WO 94/08949); the tetradentate chelates of WO 94/22816; $N_2S_2$ diaminedithiols, diamidedithiols or amideaminedithiols; $N_3S$ thioltriamides; $N_2O_2$ diaminediphenols; $N_4$ chelates such as tetraamines, macrocyclic amines or amide chelates such as cyclam, oxocyclam (which forms a neutral technetium complex) or dioxocyclam; or dithiosemicarbazones. The above described chelates are particularly suitable for technetium, but are useful for other metals also. Other suitable chelates are described in WO 91/01144, which includes chelates which are particularly suitable for indium, yttrium and gadolinium, especially macrocyclic aminocarboxylate and aminophosphonic acid chelates. Chelates which form non-ionic (i.e. neutral) metal complexes of gadolinium are known and described in U.S. Pat. No. 4,885,363. The chelate may also comprise a short sequence of amino acids such as the Cys/aminoacid/Cys tripeptide of WO 92/13572 or the peptide chelates described in EP 0719790 A2.

When the detectable moiety is a radioactive isotope of iodine, the radioiodine atom is preferably attached via a direct covalent bond to an aromatic ring, such as a benzene ring, or to a vinyl group, since it is known that iodine atoms bound to saturated aliphatic systems are prone to in vivo metabolism and hence loss of the detectable moiety.

Bone metastases may be osteoblastic (10%), osteolytic (65%) or mixed (25%) in appearance. It is believed that the compounds of the present invention are only taken up by activated osteoblasts at sites of increased bone turnover, i.e. active lesions. Such sites include areas of hyperproliferation associated with metastatic bone disease, as well as other bone pathologies. The present compounds are therefore expected to be of high diagnostic and prognostic value for osteoblastic lesions, and to allow rapid monitoring of disease and treatment progress. This is in contrast to prior art [$^{99m}$Tc]-MDP, which accumulates at sites of collagen production long after tumour cells are dead, giving no information about cell viability. The compounds of the present invention may also help to prevent the occurrence of false negative scans, via the visualisation of osteolytic lesions due to associated osteoblastic activity and allow early diagnosis of small lesions due to the specific uptake mechanism. The relatively rapid expected clearance time should allow rapid imaging and high patient throughput. The present compounds may also accumulate in fibroblasts and could hence be useful in the diagnostic imaging of sites of wound repair, and may also be useful in the diagnosis of other bone pathologies, for example osteoporosis and arthritis.

A further aspect of the present invention is the disclosure of novel ascorbic acid derivatives. These may be useful as pharmaceuticals for the treatment of tumours known to accumulate ascorbic acid, in particular bone tumours, and may also be attached to therapeutic radioisotopes or cytotoxic drugs.

Novel ascorbic acid derivatives, including those labelled with non-radioactive $^{127}$I, have been prepared, and shown to compete with $^{14}$C-labelled ascorbic acid for uptake into murine pre-osteoblast (MC3T3-E1) cells. Such derivatives have essentially identical chemical properties to the radioactive counterparts labelled with radioiodine e.g. $^{123}$I or $^{131}$I. In addition, a few known compounds have also been synthesised and shown to compete with $^{14}$C-labelled ascorbic acid for uptake into MC3T3-E1 cells. Furthermore, a $^{14}$C-labelled ascorbic acid derivative (compound 17) has been shown to accumulate in primary rat osteoblasts over a 5 hour period and remains stable over this time. Using autoradiography, accumulation has also been demonstrated in mineralised bone nodules produced by rat osteoblasts over a 21-day culture period. In vivo, the amount of $^{14}$C-compound 17 accumulating in the epiphysis of the rat 60 minutes after i.v. injection was compared to that accumulating in the diaphysis and was found to be 2.3-fold greater due to increased osteoblast activity at these sites.

The compounds of the present invention may be prepared as follows. When the detectable moiety is radioactive iodine, the substituent linked to ascorbic acid must include a non-radioactive halogen atom (to permit radioiodine exchange), an activated aromatic ring (e.g. a phenol group), an organometallic precursor compound such as a trialkyltin or trialkylsilyl, an organic precursor such as triazenes or other such moiety known to those skilled in the art. Examples of suitable substituents to which radioactive iodine can be attached are given below:

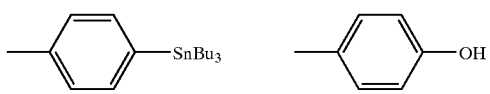

Both substituents contain groups which permit facile radioiodine substitution onto the aromatic ring. Alternative substituents containing radioactive iodine can be synthesised by direct iodination via radiohalogen exchange, e.g.

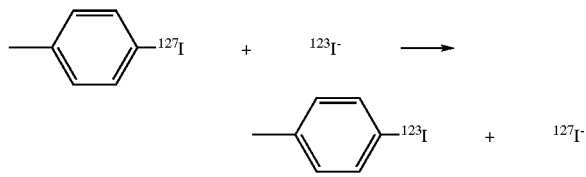

Groups for substitution of radioiodine can be attached to ascorbic acid as follows. A substituent functionalised with a carboxylic acid group can be reacted with the 6-OH of ascorbic acid to give an ester link [J. Carbohyd. Chem. 17(3) 397–404 (1998)]. Alternatively 6-bromo-6-deoxy-L-ascorbic acid [Suskovic, Croat. Chem. Acta, 58, 231 (1985)] can be reacted with an amino or thiol-functionalised substituent to give an amino [Kralj et al, Eur. J. Med. Chem., 31, 23, (1996)] or thioether [Carbohyd. Res., 134, 321, (1984)] link. 6-Amino-6-deoxy-L-ascorbic acid [Suskovic, Croat. Chem. Acta, 62, 537 (1989)] can be reacted with substituents functionalised with a carboxylic acid or an active ester to give an amide link. Persons skilled in the art will recognise that many alternative syntheses of ascorbic acid derivatives suitable for radioiodination are possible based on this disclosure.

An alternative method for synthesising ascorbic acid derivatives suitable for radioiodination involves rearrangement of a L-gulonate (shown below) under acidic conditions [Crawford et at, Adv. Carbohyd. Chem Biochem., 37, 79 (1980)].

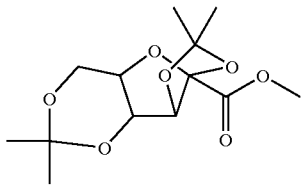

The 4,6-isopropylidene protecting group is removed and a substituent suitable for radioiodination is linked to the primary hydroxyl of the L-gulonate via an ether or ester link, for example, and the modified L-gulonate rearranged to give the corresponding ascorbic acid derivative. Alternatively the primary hydroxyl can be substituted for a bromo or amino group for reaction with an appropriately functionalised group suitable for radioiodination, prior to rearrangement to the ascorbic acid.

When the detectable moiety is a radioactive or paramagnetic metal ion, a chelating agent is attached to the ascorbate giving a chelate-ascorbic acid conjugate. Such chelate-ascorbic acid conjugates can be prepared using the bifunctional chelate approach. Thus, it is well known to prepare chelating agents which have attached thereto a functional group ("bifunctional chelates"). Functional groups that have been attached to chelating agents include: amine, thiocyanate, maleimide and active ester such as N-hydroxysuccinimide. Such bifunctional chelates can be reacted with suitable functional groups on the ascorbic acid to form the desired conjugate. Examples of chelate-amine conjugates for diaminedioxime ligands are given in WO 95/19187. In the particular case of ascorbic acid, a chelating agent can be attached at the 6-position as follows. Ascorbic acid can be reacted with a chelate-carboxylic acid conjugate to give a chelate-ascorbic acid derivative linked via an ester bond. 6-COOH-6-deoxy-L-ascorbic acid [Stuber et al, Carbohyd. Res., 60, 25 (1978)] can be reacted with a chelate-amine conjugate, or 6-NH$_2$6-deoxy-L-ascorbic acid reacted with a chelate-active ester or chelate-carboxylic acid conjugate to give chelate-ascorbic acid derivatives linked via amide bonds. 6-Br6-deoxy-L-ascorbic acid can be reacted with a chelate-amine or chelate-thiol conjugate to give either an amine or thioether link.

An alternative method for synthesising ascorbic acid derivatives involves rearrangement of an L-gulonate derivative as described above. This reaction can be used in the synthesis of chelate-ascorbic acid conjugates. A chelate can be linked to the L-gulonate using one of the methods described above and the resulting chelate-L-gulonate conjugate rearranged to give the corresponding chelate-ascorbic acid derivative. Persons skilled in the art will recognise that many alternative syntheses of chelate-ascorbic acid conjugates are possible based on this disclosure.

When the detectable moiety is a hyperpolarised atom, such as a hyperpolarised $^{13}$C atom, the desired hyperpolarised compound can be prepared by polarisation exchange from a hyperpolarised gas (such as $^{129}$Xe or $^{3}$He) to a suitable $^{13}$C-enriched ascorbic acid derivative. Both [1-$^{13}$C]- and [2-$^{13}$C]-labelled ascorbic acid derivatives are known, and have been used to examine transport and redox cycling in human erythrocytes [Himmelreich et al. Biochem. 37, 7578 (1998)]. $^{13}$C-enriched ascorbic acid derivatives can also be prepared in an analogous manner to the literature synthetic routes for $^{14}$C-labelled ascorbic acid derivatives. Thus, Hornig et al [Int. J. Vit. Nutr. Res. 42, 223 (1972) and ibid 42, 511 (1972)] have studied the autoradiographic biodistribution of [1-$^{14}$C]-L-ascorbic acid in normally fed and vitamin C deficient guinea pigs following intravenous injection. Karr et al [J. Lab. Comp., 6, 155 (1970)] have also prepared [6-$^{14}$C]-L-ascorbic acid and [5-$^{14}$C]-L-ascorbic acid from D-glucose-1-$^{14}$C and D-glucose2-$^{14}$C, respectively. Williams et al [Carbohyd. Res., 63, 149 (1978)] describe the synthesis of [4-$^{14}$C]-L-ascorbic acid from D-[3-$^{14}$C]glucopyranose and [6-$^{14}$C]-L-ascorbic acid from D-[1-$^{14}$C]glucopyranose.

Unlabelled ascorbic acid derivatives of the present invention have been tested for their ability to compete for uptake of $^{14}$C-ascorbic acid into MC3T3-E1 cells, a murine pre-osteoblast cell line. MC3T3-E1 cells are grown in tissue culture plates and the appropriate assay solution containing a standard concentration of $^{14}$C-ascorbic acid plus a competing concentration of ascorbic acid derivative added to each well. The amount of $^{14}$C-ascorbic acid taken up by the cells in 60 min is then measured.

Of compounds 11 to 15, only those containing an iodophenyl, bromophenyl or iodovinyl substituent were found to compete for uptake of $^{14}$C-ascorbic acid into MC3T3-E1 cells. Results are given in Table 10. Both Compounds 16 and 17 competed for uptake of $^{14}$C-ascorbic acid into MC3T3-E1 cells, although competition by compound 16 was very weak. Although both these compounds are known, neither has been reported in the literature to show competition with $^{14}$C-ascorbic acid for uptake into pre-osteoblast or osteoblast cells.

The present invention also relates to kits for the preparation of ascorbic acid derivatives labelled with a detectable moiety. The kits are designed to give sterile products suitable for human administration, e.g. via injection into the bloodstream. Possible embodiments are discussed below. When the detectable moiety is $^{99m}$Tc, the kit would comprise a vial containing either an ascorbic acid derivative suitable for forming a metal complex with $^{99m}$Tc or a chelate-ascorbic acid conjugate, together with a pharmaceutically acceptable reducing agent such as sodium dithionite, sodium bisulphite, formamidine sulphonic acid, stannous ion, Fe(II) or Cu(I). The reducing agent is preferably a stannous salt such as stannous chloride or stannous tartrate.

Alternatively, the ascorbic acid derivative or chelating agent-ascorbic acid conjugate could be present as the metal complex of a suitable non-radioactive metal, which, upon addition of the radiometal, undergoes transmetallation (i.e. ligand exchange) giving the desired product. The kit is preferably lyophilised and is designed to be reconstituted with sterile $^{99m}$Tc-pertechnetate ($TcO_4^-$) from a $^{99m}$Tc radioisotope generator to give a solution suitable for human administration without further manipulation.

The agents for the present invention may also be provided in a unit dose form ready for human injection and could for example be supplied in a pre-filled sterile syringe. When the detectable moiety is a radioactive isotope such as $^{99m}$Tc, the syringe containing the unit dose would also be supplied with a syringe shield (to protect the operator from potential radioactive dose).

The above kits or pre-filled syringes may optionally contain further ingredients such as buffers; pharmaceutically acceptable solubilisers (e.g. cyclodextrins or surfactants such as Pluronic, Tween or phospholipids); pharmaceutically acceptable stabilisers/antioxidants (such as gentisic acid or para-aminobenzoic acid) or bulking agents for lyophilisation (such as sodium chloride or mannitol).

The structure of compound 10 is given in Scheme 1. The structures of compounds 11 to 28 are given in Tables 1 to 4. The preparation of compounds 10–19 and 21–28 is described in Examples 1 to 6. NMR data for the compounds is given in Tables 4 to 9. The biological properties of Compounds 11 to 18 are shown in Example 7 and Table 10. The biological properties of Compound 17 are further discussed in Examples 8 and 9.

Scheme 1: Synthesis of Compound 10.

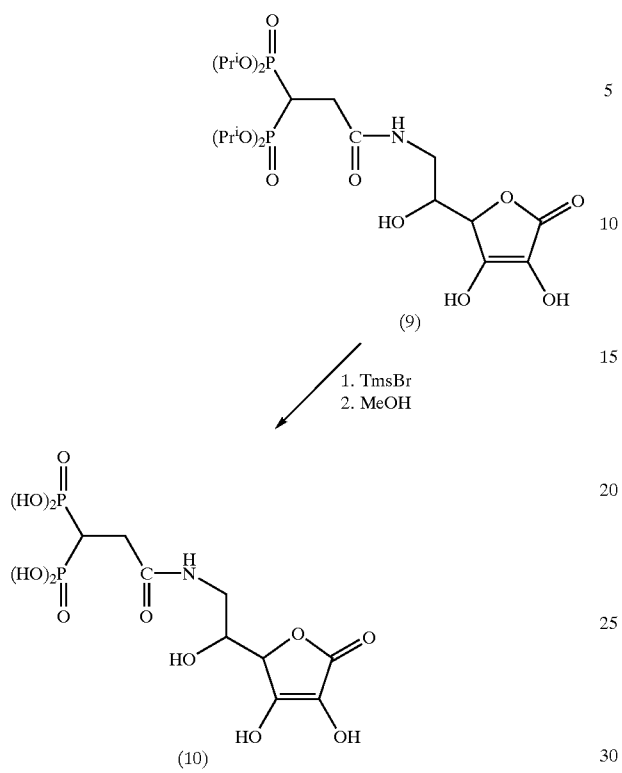

TABLE 3

Compounds 16 and 17 are literature compounds.

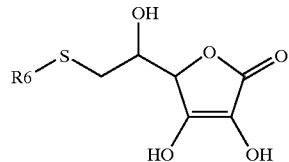

| Compound number | R⁶ |
|---|---|
| 16 | Ph— |
| 17 | PhCH₂— |
| 18 | Ph(2-COOH)— |
| 19 | HO₂C(CH₂)₂— |
| 20 | (4-MeOPh)CH₂NH(CO)CH₂— |
| 21 | [Diaminediphenol]-linker1- |
| 22 | [Diaminediphenol]-linker2- |
| 23 | [Pn216]-linker1 |
| 24 | [Pn216]-linker2 |
| 25 | [Isopropylamine]-linker1 |
| 26 | [Isopropylamine]-linker2 |
| 27 | [Hynic]-linker2 | where: [Diaminediphenol]-linkers- are:

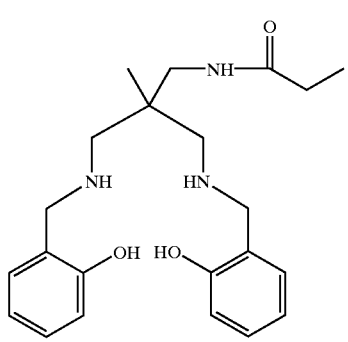

linker1

TABLE 1

| Compound | n | R² | R³ | R⁴ |
|---|---|---|---|---|
| 11 | 0 | OCH₃ | OH | H |
| 12 | 0 | H | I | H |
| 13 | 0 | H | Br | H |
| 14 | 1 | H | I | H |

TABLE 2

| Compound Number | R⁵ |
|---|---|
| 15 | 1-Iodovinyl |

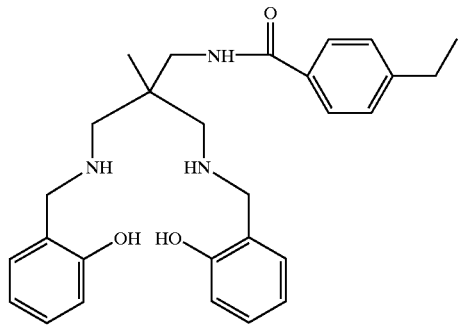

linker2 where: [Pn216]-linkers- are:

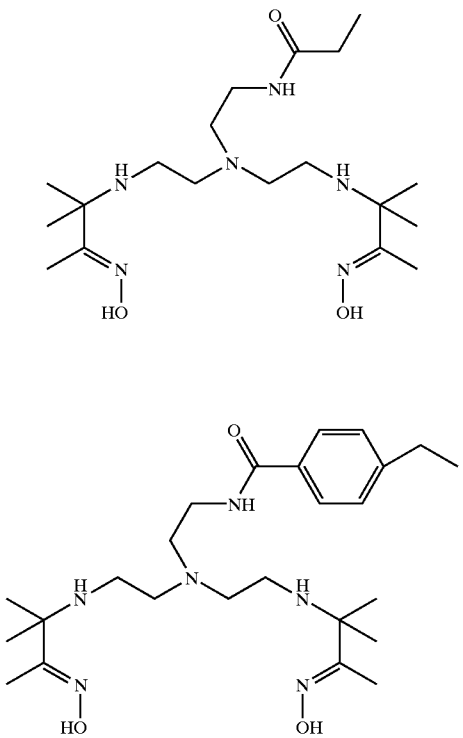

where: [Isopropylamine]-linkers- are:

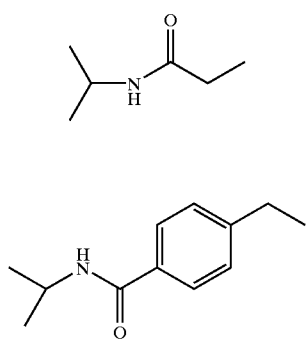

where: [Hynic]-linker- is:

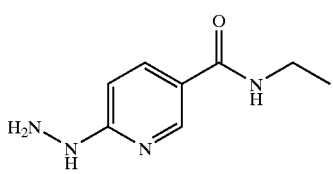

TABLE 4

| | |
|---|---|
| Compound number | R[7] |
| 28 | MAG3 | note:
the full structure of Compound 28 is given in Table 9.

EXPERIMENTAL

EXAMPLE 1

Synthesis of a Bisphosphonate Conjugate 10

$^1$H NMR chemical shifts are with respect to TMS; $^{13}$C NMR chemical shifts are with respect to $CDCl_3$ at 77 p.p.m. or, for aqueous solutions, MeOH at 49.2 p.p.m.; $^{31}$P NMR chemical shifts are with respect to external 85% $H_3PO_4$.

3,3-Bis(diisopropoxyphosphinyl)propionic acid (3)

Sodium hydride (700 mg, 0.29 mmol) was added in small portions under a stream of dry nitrogen to a vigorously stirred solution of tetraisopropyl methane-1,1-bisphosphonate (1) (5.0 gm, 14.5 mmol) in dry toluene (25 ml). After the effervescence had stopped, stirring was continued for 15 minutes. Ethylbromoacetate (3.2 gm, 19.2 mmol) was then added dropwise over a period (2 min) whereupon the flask became warm and a white precipitate began to form. Stirring was continued for a further 2 hours at room temperature. Water (20 ml) was added then carefully and the mixture vigorously stirred. The toluene layer was separated and extracted with water (20 ml). The aqueous extracts were combined, washed with ether (50 ml), acidified to pH 1 and re-extracted with dichloromethane (2×25 ml). The dichloromethane extracts were combined, dried ($MgSO_4$), filtered and solvent evaporated under reduced pressure to leave the acid (3) as a pale yellow liquid (800 mg). The toluene layer was also dried ($MgSO_4$), filtered, and solvent evaporated to leave an oil which was found to be the ethyl ester (2) and unreacted starting material. This oil was dissolved in a methanol:water mixture (20 ml, 3:1) containing lithium hydroxide (1 g, 24 mmol) and the solution stirred at room temperature for 16 h. The methanol was removed by evaporation and water (20 ml) was then added. This aqueous solution was washed with ether (2×20 ml), acidified to pH 1 with dilute HCl and then extracted with dichloromethane (2×25 ml). The dichloromethane extracts were combined, dried ($MgSO_4$), filtered and volatile components removed under reduced pressure to leave the acid (3) (2.77 g) as a pale yellow liquid. The combined product (3) (3.57 g, 61%) was sufficiently pure to be used in subsequent reactions without further purification.

$\delta_P(CDCl_3)$ 21.79

$\delta_C(CDCl_3)$ 23.7 (m), 30.6 (s), 34.0 (t, $J_{PC}$=138 Hz), 71.8 (m), 172.8 (s)

(N-Succinimidyl) 3,3-Bis(bisisopropoxyphosphinyl) Propionate (4)

A solution of dicyclohexylcarbodiimide (2.0 g, 9.71 mmol) in dichloromethane (10 ml) was added in one portion to a stirred solution of 3,3-bis(bisisopropoxy-phosphinyl) propionic acid (3) (3.57 g, 8.88 mmol) and N-hydroxysuccinimide (1.15 g, 10 mmol) in dry dichloromethane (35 ml). After about 10 minutes a white precipitate of dicyclohexylurea began to appear. The mixture was stirred for 16 h and the solid formed was filtered off and washed with dichloromethane (15 ml). The solvent was removed under reduced pressure from the combined dichloromethane solutions to leave a viscous residue, which was shown by NMR to be the title compound in a good state of purity. Final purification of this residue was carried out using chromatography on silica with a dichloromethane:methanol mixture (19:1) as eluant. The product (4.0 g, 91%) ($R_f$ 0.2) was isolated as a viscous oil.

$\delta_P$(CDCl$_3$) 20.0

$\delta_H$(CDCl$_3$) 1.25–1.31 (24H, m, CH$_3$×8), 2.77 (4H, s, CH$_2$× 2), 2.83 (1H, m, CH), 2.7–3.1 (2H, m, CH$_2$), 4.37 (4H, dq, $J_{HH}$=6 Hz, $J_{PH}$=13.5 Hz, CH×4)

(R)-5-(2-azido-(S)-1-hydroxyethyl)-3,4-dibenzyloxy-5H-furan-2-one (6)

(R)-5-[2-(4-methylphenylsulfonyloxy)-(S)-1-hydroxyethyl]-3,4dibenzyloxy-5H-furan-2-one (5)† (550 mg, 1.1 mmol), sodium azide (190 mg, 1.7 mmol) and methanol (2 ml) were heated under reflux for 6 hours. The reaction mixture was cooled and most of the solvent removed by evaporation at room temperature. The resulting material was partitioned between water (25 ml) and dichloromethane (25 ml) and the aqueous phase extracted with dichloromethane (25 ml). The combined organic fractions were dried (MgSO$_4$), filtered and volatile components evaporated under reduced pressure (8 mm/Hg) at room temperature to give the product (6) as a yellow waxy solid (375 mg, 89%). This material was used without further purification.

$\delta_H$(CDCl$_3$) 3.22 (1H, dd, J=6 and 12.5 Hz, CH$_2$N$_3$), 3.40 (1H, br d, OH), 3.46 (1H, dd, J=7 and 12.5 Hz, CH$_2$N$_3$), 3.88 (1H, br m, CHO), 4.55 (1H, d, J=2 Hz , CHO ring), 4.95 (2H, br s, OCH$_2$), 5.03 (1H, d, J=12 Hz, OCH), 5.08 (1H, d, J=12 Hz, CHO), 7.12 (2H, m, Ar), 7.21–7.31 (8H, m, Ar)

† V. F. Dallacker and J. Sanders, *Chem. Zeit.*, 1985, 109, 197–202

(R)-5-(2-amino-(S)-1-hydroxyethyl)-3,4-dibenzyloxy-5H-furan-2-one (7)

Triphenylphosphine (600 mg, 2.4 mmol) was added to a stirred solution of (R)-5-(2-azido-(S)-1-hydroxyethyl)-3,4-dibenzyloxy-5H-furan-2-one (5) (750 mg, 2 mmol) in THF (10 ml) and after a few minutes gas was evolved. The stirring was continued until the effervescence had ceased (typically 2–3 h) and water (2 ml) was then added and the mixture stirred for a further 1 hour. The THF was removed under reduced pressure and the residue partitioned between dichloromethane (25 ml) and water (25 ml). The organic phase was separated, dried (MgSO$_4$), filtered and any volatile components evaporated under reduced pressure (45° C. at 8 mm/Hg) to leave a viscous orange residue which was purified by chromatography on silica. Initial elution with a dichloromethane:methanol (19:1) mixture removed the less polar by-products and the product was then isolated by elution with a dichloromethane:methanol (3:1) mixture as a pale yellow oil (150 mg; 21%) ($R_f$ 0.25).

$\delta_H$(CDCl$_3$) 2.49 (3H, br s, NH$_2$ and OH), 2.76 (1H, dd, J=5 and 13 Hz, NCH), 2.83 (1H, dd, J=7 and 13 Hz, NCH), 3.70 (1H, m, CHO), 4.47 (1H, d, J=2 Hz, CHO ring), 4.98 (2H, s, OCH$_2$), 5.05 (1H, d, J=12 Hz, OCH), 5.11 (1H, d, J=12 Hz, CHO), 7.10–7.17 (2H, m, Ar), 7.20–7.32 (8H, m, Ar)

(R)-5-(3-aza-6.6-bis(bisisopropoxyphosphinyl)-(S)-1-hydroxy-oxo-hexyl)-3,4-dibenzyloxy-5H-furan-2-one (8)

(R)-5-(2-amino-(S)-1-hydroxyethyl)-3,4-dibenzyloxy-5H-furan-2-one (7) (180 mg, 0.5 mmol) in dry dichloromethane (1 ml) was added in one portion to a stirred solution of (N-succinimidyl) 3,3-bis(bisisopropoxyphosphinyl)propionate (4) (250 mg, 0.5 mmol) in dry dichloromethane (1 ml), whereupon crystals of N-hydroxysuccinimide began to precipitate. The mixture was stirred for 30 min, dichloromethane (10 ml) was then added and the solution washed with water (2×10 ml). The organic phase was then dried (MgSO$_4$), filtered and solvent evaporated under reduced pressure to leave (8) as a pale yellow viscous oil in a virtually pure state. Final purification could be achieved by chromatography on silica with a dichloromethane:methanol mixture (19:1) as the eluant. The product (8) (180 mg, 49%) ($R_f$ 0.25) was obtained as a pale yellow viscous oil.

$\delta_P$(CDCl$_3$) 21.9 (d, $J_{PP}$=4 Hz), 22.0 (d, $J_{PP}$=4 Hz)

Mass Spec (FABS), Calculated for C$_{35}$H$_{52}$NO$_{12}$P$_2$ 740.2965 (M+H)$^+$, found 740.2965.

(R)-5-(3-aza-6,6-bis(bisisopropoxyphosphinyl)-(S)-1-hydroxy-4-oxo-hexyl)-3,4-dihydroxy-5H-furan-2-one (9)

A solution of (R)-5-(3-aza-6,6-bis(bisisopropoxyphosphinyl)-(S)-1-hydroxy-4-oxo-hexyl)-3,4-dibenzyloxy-5H-furan-2-one (8) (700 mg, 0.96 mmol) in methanol (10 ml) was hydrogenated over a palladium catalyst (200 mg, 10% Pd/C) and in a hydrogen atmosphere (30 atm) for 2 hours at room temperature. The catalyst was removed by filtration through Celite and the filter cake washed with methanol (50 ml). These washings were combined with the methanol filtrate and the volatile components evaporated under reduced pressure to leave (9) as a viscous oil in a good state of purity. The residue was purified by chromatography on silica using an ethyl acetate;methanol (9:1) mixture as the eluant. The pure product (9) (50 mg, 9%) ($R_f$ 0.3) was isolated as a cream coloured solid.

$\delta_P$(CDCl$_3$) 21.8 (br s), 22.98 (br s)

Mass Spec (FABS), Calculated for C$_{21}$H$_{40}$NO$_{12}$P$_2$ 560.2026 (M+H)$^+$, found 560.2026.

6-[(R)-5-(2,5-dihydro-3,4-dihydroxy-2-oxo-furan-5-yl)]-4-aza-(S)-6-hydroxy-3-oxo-hexane-1,1-bisphosphonic acid (10)

To a solution of (R)-5-(3-aza-6,6-bis(bisisopropoxyphosphinyl)-(S)-1-hydroxy4-oxo-hexyl)-3,4-dihydroxy-5H-furan-2-one (9) (370 mg, 0.6 mmol) in dichloromethane (10 ml) was added bromotrimethylsilane (1 g, 6.4 mmol). The mixture was heated under reflux for 6 h and the solvent was then removed under reduced pressure. Methanol (25 ml) was added and volatile components evaporated under reduced pressure. This process was repeated twice to leave a brown residue. The product (10) was purified by reverse phase HPLC on a C$_{18}$ column using aqueous methanol (50%) as eluant and isolated as a pale brown solid (120 mg; 46%).

$\delta_P$(D$_2$O) 21 (br)

$\delta_C$(D$_2$O) 32.1 (br s), 34.8 (t, $J_{PC}$=138 Hz), 42.1 (s), 67.1 (s), 76.8 (s), 118.1 (s), 155.5 (s), 173.4 (s), 173.5 (br s).

EXAMPLE 2

Synthesis of Compounds 11 to 15

Compounds 11 to 15, all esters of ascorbic acid, were synthesised directly from ascorbic acid and the corresponding carboxylic acid using the method reported by Gan et al [J. Carbohyd. Chem., 17, 397–404 (1998)]. Compounds 11 and 13 to 15 were all synthesised using a similar procedure to that given below for 6-O-(4-iodobenzoyl)-L-ascorbic acid (Compound 12):

4-Iodobenzoic acid (0.5 g, 2.48 mmol), and L-ascorbic acid (2 g, 11.3 mmol) were mixed and stirred in concentrated sulphuric acid (10 ml) for 24 hrs at room temperature. The reaction was quenched by the addition of ice and solid sodium chloride. The mixture was extracted with ethyl acetate and the organic layer dried over magnesium sulphate. The title compound was isolated by evaporation under reduced pressure followed by crystallisation from a chloroform/hexane mixture and drying under vacuum (200 mg, 5.6 mmol).

EXAMPLE 3

Synthesis of Compounds 16 and 17

These compounds were synthesised using methods similar to the literature procedures, [Carbohyd. Res., 134, 321, (1984)] for compound 16 and [J. Biol. Chem., 271, 26032, (1996)] for compound 17. $^{14}$C-compound 17 was prepared using a similar method but starting with $^{14}$C-bromo ascorbic acid.

EXAMPLE 4

Synthesis of Compounds 18 and 19

These compounds were synthesised using very similar methods. To a suspension of sodium carbonate (960 mg) in methanol (2 ml) and water (6 ml) was added 6-bromo-L-ascorbic acid (500 mg) and thiosalicyclic acid (350 mg; for compound 18) or 3-mercaptoproprionic acid (240 mg; for compound 19). The resulting mixture was stirred for at least 4 hr at room temperature and the reaction checked for completion by TLC. The reaction was acidified using 2M HCl and the product extracted into ethyl acetate. The organic layer was washed with brine and dried over MgSO$_4$. Filtration and evaporation to dryness yielded a buff-coloured solid which was treated with chloroform and filtered to yield 590 mg compound 18/200 mg compound 19.

EXAMPLE 5

Synthesis of Compounds 21–27

Compound 21

The trityl protected acid was prepared by a method described in, [Inorg. Chem 23 (23) 3795–3797 (1984)]. S-trityl mercapto acetic acid (5.6 g) was dissolved in dry acetonitrile (60 ml) under nitrogen. To this was added a solution of N-hydroxysuccinimide (2 g) in acetonitrile (10 ml). This was followed by the addition of DCC (4.4 g) in acetonitrile (20 ml). The mixture was stirred overnight at room temperature. The product was isolated by filtration followed by evaporation of the filtrate to give a white solid (6 g). The S-trityl-mercaptoacetic acid NHS ester (400 mg) was dissolved in dry dichloromethane (10 ml) under nitrogen. To this was added the diaminodiphenol ligand (300 mg), followed by triethylamine (146 μl). The reaction was stirred at room temperature overnight and the product isolated by evaporation followed by flash column chromatography on silica. The trityl protected Diaminodiphenol-linker (270 mg) was dissolved in DCM (6 ml) to this was added triethylsilane (100 μl) followed by trifluoroacetic acid (300 μl). The mixture was stirred for 4 hrs at room temperature, after which it was evaporated to dryness and used directly in the final step, which was carried out as described for compounds 18 and 19.

Compounds 22–27 were prepared in an analogous manner.

EXAMPLE 6

Synthesis of Compound 28

This compound was synthesised using a combination of methods described in the literature. The chelate MAG3 was prepared using the method described by Winnard et al [Nucl Med Biol 24 425–432 (1997)]. N-methyl-6-amino-6deoxy-O$^3$-benzyl-L-ascorbic acid was prepared by a method described by Kralj M et al [Eur J Med Chem 31 23–35 (1996). The coupling reaction between MAG3 and the N-methyl6-amino-6-deoxy-O$^3$-benzyl-L-ascorbic acid was achieved using PyBrop (an agent specifically used for N-methyl amines) in a manner similar to that described by Coste J [Tet. Lett. 32 (17) 1967–1970 (1991). Thus, to N-methyl-6-amino-6-deoxy-O$^3$-benzyl-L-ascorbic acid (91 mg, 3.26×10$^{-4}$ moles) in dry DMF (5 ml) under nitrogen was added MAG3 (100 mg, 3.26×10$^{-4}$ moles). While stirring at room temperature, diisopropylethylamine (211 mg, 1.63×10$^{-3}$ mol) was added followed by PyBrop (182.5 mg, 3.914×10$^{-4}$ mol). After stirring overnight the solvent was removed in vacuo and the product isolated by preparative HPLC.

TABLE 5

$^1$H NMR Data for compounds 11, 12, 13 and 14.

| NMR data (ppm) | Compound 11 | Compound 12 | Compound 13 | Compound 14 |
|---|---|---|---|---|
| R$^2$ | 3.8 | — | — | — |
| R$^3$ | — | — | — | — |
| R$^4$ | — | — | — | — |
| (CH$_2$)n | — | — | — | 3.57 |
| H5 | 3.77 | 4.85 | 4.07 | 3.98 |
| H6$_b$ | 4.12 | 4.45 | 4.20 | 4.12 |
| H6$_a$ | 4.32 | 4.65 | 4.28 | 4.18 |
| H4 | 4.72 | 4.85 | 4.66 | 4.56 |
| Aryl | 6.6–7.5 | 8.0–7.5 | 7.7–7.0 | 7.5–7.05 |

TABLE 6

$^1$H NMR Data for compound 15.

| NMR data (ppm) | Compound 15 |
|---|---|
| H-5 | 3.7 |
| H-6$_{a,b}$ | 4.2 |
| H-4 | 4.28 |
| I-vinyl$_a$ | 6.83 |
| I-vinyl$_b$ | 6.22 |

TABLE 7

$^1$H NMR Data for Compounds 16 and 17.

| NMR data (ppm) | Compound 17 | Compound 16 |
|---|---|---|
| CH$_2$ | 2.70 | |
| CH$_2$(H-6$_{a,b}$) | 3.67 | 3.22–3.26 |
| CH(H-5) | 3.83 | 3.95–3.99 |
| CH(H-4) | 4.35 | 4.88 |
| Aryl | 7.13–7.18 | 7.20–7.44 |

TABLE 8

$^1$H NMR Data for compounds 21–27

| Cmpd number | ppm | ppm | ppm | ppm | Ppm | ppm | ppm | ppm |
|---|---|---|---|---|---|---|---|---|
| 21 | 1.2 s,3-H | 2.6 d,2-H | 3.0 s,4-H | 3.5 m,4-H | 4.0 m,1-H | 4.6 m,4-H | 4.8 d,1-H | 6.6–7.3 m,8-H |
| 22 | 0.7 s,3-H | 2.1 m,2-H | 2.5 m,4-H | 2.9 s,2-H | 3.3–3.4 m,3-H | 3.8 s,4-H | 4.3 d,1-H | 6.3–7.3 m,12-H |
| 23 | 1.5 s,12-H | 1.9 s,6-H | 2.2–2.9 m,4-H | 3.0–3.1 m,4-H | 3.2–3.3 m,4-H | 3.3–3.4 m,4-H | 4.0 m,1-H | 4.8 d,1-H |
| 24 | 1.5 s,12-H | 1.8 s,6-H | 2.5–3.0 m,12-H | 3.5 s,1-H | 3.8 s,1-H | 4.0 m,1-H | 4.5 s,1-H | 7.4–7.9 m,4-H |
| 25 | 0.7 d,6-H | 2.4 d,2-H | 2.8 d,2-H | 3.6 m,2-H | 4.3 d,1-H | | | |
| 26 | 1.3 d,6-H | 2.2 d,2-H | 3.7 d,2-H | 3.8 m,1-H | 4.1 m,1-H | 4.4 d,1-H | 7.4 d,2-H | 7.6 d,2-H |
| 27 | 1.8 s,9-H | 2.7 m,4-H | 3.5 t,2-H | 3.9 m,1-H | 4.8 d,1-H | 7.0 d,1-H | 8.2 dd,1-H | 8.4 d,1-H |

TABLE 9

$^1$H NMR Data for compound 28

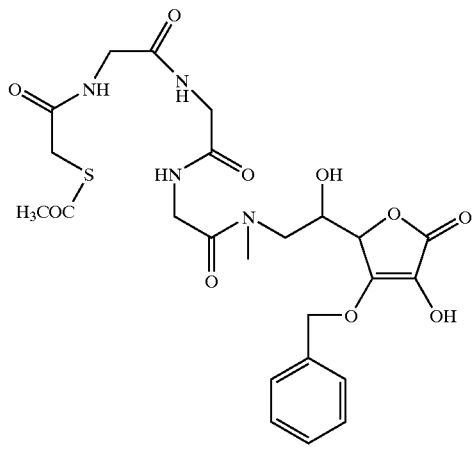

| NMR data(ppm) | Compound 28 |
|---|---|
| SCOCH3 | 2.3 |
| NCH3 | 3.0 |
| SCH2 | 3.3 |
| CH2(H-6$_{a,b}$) | 3.4–3.6 |
| Amide-CH2 | 3.6 |
| Amide CH2x2 | 3.9 |
| CH(H-5) | 4.1 |
| CH(H-4) | 4.6 |
| Benzyl-CH2 | 5.5 |
| Aryl | 7.4 |

EXAMPLE 7

Standard Cell Uptake Assay

Solutions and Reagents

Transport buffer: 134 mM NaCl, 5.4 mM KCl, 1.8 mM CaCl$_2$, 0.8 mM MgSO$_4$, 20 mM HEPES, 10 mM glucose, pH7.3, stored at room temperature Assay buffer: Transport buffer+40 µM homocysteine $^{14}$C-ascorbic acid (Amersham Pharmacia Biotech)

Stock solution: 50 µCi in 50 µl Analar water, stored at −20° C.

Assay solution: 200 nCi $^{14}$C-ascorbic acid in 200 µl assay buffer/well (125 µM)

Ascorbic acid (Sigma)

Dehydroascorbic acid (Sigma)

Test Compounds

Stop buffer: 200 µM phloretin in assay buffer, chilled to 4° C.

Lysis solution: 0.1% SDS in Analar water

Method

MC3T3-E1 murine pre-osteoblast cells were seeded in a 24-well plate at 2×10$^5$ cells/well in 1 ml minimal essential media plus 10% FCS, penicillin and streptomycin. Cells were grown overnight at 37° C., 5% CO$_2$. Assay buffer and solutions were prepared on the morning of the assay. Cells were examined under the microscope for confluence and viability. Growth media was removed using a Liquipippette and each well washed with 2×200 µl assay buffer. The appropriate assay solution was added to each well and the plate incubated at 37° C. for the required time. To stop the reaction, 0.5 ml chilled stop buffer was added to each well. Each well was then washed with 0.5 ml stop buffer. Cells were lysed in 0.1% SDS solution for approximately 10 min and solutions transferred to scintillation vials. Each well was then washed with assay buffer and this wash solution also transferred to the appropriate scintillation vial. Scintillation fluid (5 ml) was added to each vial, the vials vortexed and counted on a Rackbeta counter.

TABLE 10

Results of cell assay

| Compound | Competition | IC50 (µM) |
|---|---|---|
| Ascorbic acid | Yes | 258 |
| 11 | No | — |
| 12 | Yes | 384 |
| 13 | Yes | 279 |
| 14 | Yes | 1880 |
| 15 | Yes | 796 |
| 16 | Yes | 1847 |
| 17 | Yes | 108 |
| 18 | No | — |
| 19 | Not tested | — |

EXAMPLE 8

Uptake of $^{14}$C-Compound 17 into Rat Osteoblasts

Preparation and Culture of Primary Rat Osteoblasts

Foetus heads were collected and sprayed with 70% isopropanol. Calvaria were then removed by cutting the skin from the top of the head, making one incision through the calvaria from the external auditory meatus across behind the parietal bones and a second forward to above the eye sockets. When all the calvaria were isolated, they were rinsed with PBS ($Ca^{2+}$ and $Mg^{2+}$-free), then incubated in trypsin at 37° C. for 10 minutes. Calvaria were transferred into 0.2% collagenase (type II) in HBSS for 30 minutes at 37° C. This collagenase digestion was repeated for 60 minutes to release the osteoblast populations. Supernatant was removed and spun down to obtain a cell pellet. The pellet was resuspended in media, viable cells counted and plated out into a T75 flask. Once confluent, cells were subcultured into 6-multiwell plates at $2\times10^4$–$2\times10^5$ cells/well in 3 ml medium containing 1 mM β-glycerophosphate. In addition ascorbic acid (50 μg/ml), $^{14}$C-ascorbic acid (19.6 μCi/ml) or $^{14}$C-compound 7 (2.8 μCi/ml) were incubated with osteoblasts over the culture period. Cells were fed two to three times per week and cultured for up to 21 days. Nodules became macroscopically visible at around 7–10 days and commenced mineralisation (assessed by Alizarin red staining) soon after.

Autoradiography

At the end of the culture period, cells were fixed with 2.5% glutaraldehyde and dehydrated with an increasing series of ethanol concentrations. Approximately 2 ml of hypercoat emulsion (LM-1; APB) was added to each well and incubated at room temperature in the dark for 24–36 hours. The emulsion was then developed following standard methods.

HPLC Analysis

The separation of DHAA, M, compound 7 and Benzyl Mercaptan was successfully completed using the following HPLC profile:

Mobile phase: A and B=50% acetonitrile:50% 50 mM $KH_2PO_4$
Detector: UV (235 nm)/Flow Scintillation Analyser (β-radiation)
Flow rate: 1 ml/min
Column: Waters Spherisorb S5NH2—5 μm—4.6×250 mm

| (y = mV.min & x = nmoles) | Retention Time (min) | Calibration Graph |
|---|---|---|
| DHAA | 3.34 ± 0.10% | y = 121946 nmoles |
| AA | 5.74 ± 0.20% | y = 215320 nmoles |
| Compound 7 | 3.71 ± 0.27% | y = 255088 nmoles |
| Benzyl Mercaptan | 2.44 ± 0.14% | y = 78710 nmoles |

$^{14}$C-compound 7 samples analysed using the HPLC profile above were:
MEM solution (standard)
0.1%SDS solution (standard)
MEM-Removed from cells
0.1% SDS - Lysed cells, at time points of 1, 3, 5, 24, 48, 72, 96 and 168 hrs.

Results

The HPLC results showed evidence of peak activity within the cells up to 5 hrs indicating the presence of $^{14}$C-compound 17. The other time periods gave no peaks as the signal to noise ratio was too low which indicates that $^{14}$C-compound 17 has been broken down within the cell. 0.1% SDS was used as a test to see if the extraction process from the cells caused the degradation of $^{14}$C-compound 17. The analysis of $^{14}$C-compound 17 in MEM and SDS however showed that it is quite stable within these solutions up to 5 hrs.

The conclusion can be reached that $^{14}$C-compound 17 is stable enough within these environmental conditions to have been taken up within the cells and is consequently broken down.

Autoradiography experiments demonstrate that both $^{14}$C-ascorbic acid and $^{14}$C-compound 17 are associated with the mineralising nodules and not the surrounding confluent osteoblast monolayer.

EXAMPLE 9

In Vivo Biodistribution of $^{14}$C-compound 17

Method

Three rats were anaesthetised with halothane and injected with 0.2 ml $^{14}$C-compound 17 in PBS (4 μCi total dose; specific activity 5 mCi/mmol). After 60 minutes, the rats were sacrificed by cervical dislocation. Tissues were placed into pre-weighed glass scintillation vials and 3 ml toluene added. Samples were incubated overnight at 50° C. Samples were then decolourised with 0.1 ml Na-EDTA:0.5 ml $H_2O_2$ overnight at 50° C. Finally 10 ml Hionic-Fluor (Packard) was added to each vial and samples counted on a LKB scintillation counter.

Results

In this preliminary study, most of the activity was present in the blood, liver and kidneys after 60 minutes. Measurement of activity present in the femur showed 0.041% id/g in the diaphysis and 0.095% id/g in the epiphysis, a ratio of 2.3 demonstrating greater uptake into the actively growing tips of the bone.

HPLC analysis showed the compound to be stable in plasma, hence it is likely that the uptake seen is due to intact $^{14}$C-compound 17.

What is claimed is:

1. A compound comprising:

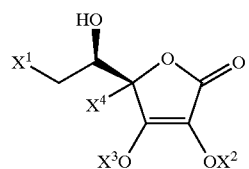

wherein: $X^1$ is OH or SH or $NH_2$ or —L-Z;
$X^2$ and $X^3$ are the same or different and each is H, $C_{1-4}$ alkyl, $C_{1-4}$ fluoroalkyl, benzyl, a protecting group or —L-Z;
$X^4$ is H or $C_{1-4}$ alkyl;
L is a linker comprising a chain of 0–10 atoms;
Z is a group comprising a detectable moiety that excludes $^3$H, $^{14}$C, $^{18}$F, and $^{11}$C;
and wherein when neither of X2 or X3 is —L-Z that the compound further includes at least one detectable moiety.

2. The compound of claim 1, wherein the detectable moiety comprises a metal complex of a chelating agent.

3. The compound of claim 1, wherein the detectable moiety is a radionuclide.

4. The compound of claim 3, wherein the radionuclide is a gamma emitter.

5. The compound of claim 4, wherein the gamma emitter is $^{99m}$Tc or $^{123}$I.

6. The compound of claim 3, where the radionuclide is $^{123}$I, $^{125}$I or $^{131}$I and Z is an iodovinyl group, or an iodo-$C_{5-12}$-aryl group.

7. The compound of claim 1, where the detectable moiety is a hyperpolarised atom.

8. The compound of claims 1, wherein $X^1$ is —L-Z.

9. The compound of claims 1, wherein L is a linker group which comprises a 0–10 atom chain and has the formula $(A)_m$
where A is —$CR_2$—, —CR=CR—, —C≡C—, —NRCO—, —CONR—, —O(CO)—, —(CO)O—, —$SO_2NR$—, —$NRSO_2$—, —$OCR_2$—, —$SCR_2$—, —$NRCR_2$—, a $C_{4-8}$ cycloheteroalkylene group, a $C_{4-8}$ cycloalkylene group, a $C_{5-12}$ arylene group or a $C_{3-12}$ heteroarylene group;

m is an integer of value 0 to 10;

each R group is independently chosen from H, $C_{1-4}$ alkyl, $C_{1-4}$ alkenyl, $C_{1-4}$ alkynyl, $C_{1-4}$ alkoxyalkyl or $C_{1-4}$ hydroxyalkyl.

10. The compound of claim 9, wherein the linker group comprises a 0–4 atom chain.

11. The compound of claims 1, of formula:

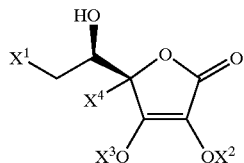

with $X^1$–$X^4$, L and Z as defined in claim 1.

12. The compound of claim 11, wherein each of $X^2$ and $X^3$ is H.

13. A method of diagnosing metastatic bone disease using compound of claim 1, comprising:

providing a unit dose of the compound;

injecting a unit dose into a patient; and imaging said patient to identify uptake of compound by activated osteoblasts at sites of increased bone turnover.

14. A method of using the compound of claim 1 in the radiotherapy of metastatic bone disease, comprising:

providing a unit dose of the compound;

injecting a unit dose into a patient; and delivering a local targeted radioactive dose to activated osteoblasts at sites of increased bone turnover.

* * * * *